(12) United States Patent
Thompson

(10) Patent No.: US 6,324,426 B1
(45) Date of Patent: Nov. 27, 2001

(54) POWER CONSUMPTION REDUCTION IN MEDICAL DEVICES EMPLOYING MULTIPLE SUPPLY VOLTAGES AND CLOCK FREQUENCY CONTROL

(75) Inventor: David L. Thompson, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/703,166

(22) Filed: Oct. 31, 2000

Related U.S. Application Data

(60) Division of application No. 09/181,517, filed on Oct. 28, 1998, now abandoned, which is a continuation-in-part of application No. 09/067,881, filed on Apr. 28, 1988, now abandoned.

(51) Int. Cl.[7] .................................................. A61N 1/362
(52) U.S. Cl. ................................................................ 607/16
(58) Field of Search ................................. 607/1, 2, 4, 5, 607/9, 16

(56) References Cited

U.S. PATENT DOCUMENTS

| | | |
|---|---|---|
| 4,031,899 | 6/1977 | Renirie . |
| 4,407,288 * | 10/1983 | Langer et al. .......................... 607/16 |
| 4,460,835 | 7/1984 | Masuoka . |
| 4,561,442 | 12/1985 | Vollman et al. . |
| 4,791,318 | 12/1988 | Lewis et al. . |
| 5,022,395 | 6/1991 | Russie . |
| 5,154,170 | 10/1992 | Bennett et al. . |
| 5,185,535 | 2/1993 | Farb et al. . |
| 5,388,578 | 2/1995 | Yomtov et al. . |
| 5,610,083 | 3/1997 | Chan et al. . |
| 5,916,237 | 6/1999 | Schu . |
| 6,029,087 | 2/2000 | Wohlgemuth . |

OTHER PUBLICATIONS

Mulder, Jan et al. Application of the Back Gate in MOS Weak Inversion Translinear Circuits, *IEEE Transactions on Circuits and Systems–I: Fundamental Theory and Applications*, vol. 42, No. 11 (Nov. 1995).

* cited by examiner

*Primary Examiner*—George R. Evanisko
(74) *Attorney, Agent, or Firm*—Girma Wolde-Michael; Reed A. Duthler

(57) ABSTRACT

Power consumption in medical devices is reduced through the operation of circuits at clock speeds of lower levels to adequately complete desired functions during predetermined time periods (e.g., blanking interval, upper rate interval, etc.) just-in-time prior to subsequent required functional processes; by providing supply voltages tailored for various circuits of an integrated circuit; by operating two or more circuits of an integrated circuit at different clock frequencies; by changing the supply voltage level "on the fly" as required by specific circuit timing functions required for various circuitry based on clock frequencies used to control operation of such circuitry; and/or by tailoring back gate bias or adjusting back gate bias "on the fly" for circuits based on the supply voltage level applied to the circuits.

10 Claims, 10 Drawing Sheets

POWER CONSUMPTION REDUCTION IN MEDICAL DEVICES EMPLOYING MULTIPLE SUPPLY VOLTAGES AND CLOCK FREQUENCY CONTROL

CLAIM TO PROIRITY AND REFERENCE TO RELATED APPLICATIONS

This application is a Continuation-In-Part, and claims priority and other benefits from the filing date, of U.S. patent application Ser. No. 09/067,881 for "Power Consumption Reduction in Medical Devices Using Multiple Supply Voltages and Clock Frequency Control" to Thompson, filed Apr. 29, 1998, hereby incorporated by reference herein in its entirety.

This application is a division of prior application No. 09/181,517 filed Oct. 28,1998 which is a continuation in part of Ser. No. 09/067,881 filed Apr. 28, 1988, now abandoned.

FIELD OF THE INVENTION

The present invention relates to power consumption of integrated circuit to designs such as circuits used in medical devices, particularly implantable devices. More particularly, the present invention pertains to providing adjustable clock control and/or multiple supply voltage levels for operation of such circuits.

BACKGROUND OF THE INVENTION

Various devices require operation with low power consumption. For example, hand-held communication devices require such low power consumption and, in particular, implantable medical devices require low power capabilities. With respect to implantable medical devices, for example, microprocessor-based implantable cardiac devices, such as implantable pacemakers and defibrillators, are required to operate with a lower power consumption to increase battery life and device longevity.

Generally, such low power devices are designed using complementary metal oxide semiconductor (CMOS) technology. CMOS technology is general used because such technology has the characteristic of substantially zero "static" power consumption.

Power consumption of CMOS circuits consists generally of two power consumption factors, namely "dynamic" power consumption and static power consumption. Static power consumption is only due to current leakage as the quiescent current of such circuits is zero. Dynamic power consumption is the dominant factor of power consumption for CMOS technology. Dynamic power consumption is basically due to the current required to charge internal and load capacitances during switching, i.e. the charging and discharging of such capacitances. Dynamic power (P) is equal to: $\frac{1}{2}CV_{DD}^2 F$, where C is nodal capacitance, F is the clock or switching frequency, and $V_{DD}$ is the supply voltage for the CMOS circuit. As can be seen from the formula for calculating dynamic power (P), such dynamic power consumption of CMOS circuits is proportional to the square of the supply voltage ($V_{DD}$). In addition, dynamic power (P) is proportional to the switching or clock frequency (F).

In accordance with the formula for dynamic power consumption, it has been effective conventionally in CMOS integrated circuit designs to scale down the supply voltage for an entire device (e.g. hybrid) or integrated circuit (IC), i.e., operate the circuit at low supply voltages, to reduce power consumption for such designs. For example, in the MEDTRONIC SPECTRAX® product of circa 1979, IC circuitry was powered by one lithium iodine (as opposed to the two cells employed in the prior art). This reduced the supply voltage to 2.8 volts from 5.6 volts, thus reducing overhead current. Voltages required to be greater than 2.8 volts were generated by a voltage doubler, or alternatively by a charge pump (e.g., output pacing pulses). In the MEDTRONIC SYMBIOS® product of circa 1983, for example, logic circuitry was powered by a voltage regulator controlling the IC supply voltage to a "sum of thresholds" supply. This regulator provided a supply to the IC (i.e., $V_{DD}$) of several hundred millivolts above the sum of the n-channel and p-channel thresholds of the CMOS transistors making up the IC. This regulator was self calibrating regarding manufacturing variations of the transistor thresholds.

Other devices reduced power consumption in other manners. For example, various device designs have shut-down analog blocks and/or shut-off clocks to logic blocks not being used at particular times, thereby reducing power. Microprocessor based devices have historically used a "burst clock" design to operate a microprocessor at a very high clock rate (e.g., generally 500–1000 Kilohertz (KHz)), for relatively short periods of time to gain the benefit of a "duty cycle" to reduce average current drain. A much lower frequency clock (e.g., generally 32 KHz) is used for other circuitry and/or the processor when not in the high clock rate mode, i.e., burst clock mode. Many known processor based implanted devices utilize the burst clock technique. For example, implanted devices available from Medtronic. Vitatron, Biotronic, ELA, Intermedics, Pacesetters, InControl, Cordis, CPI, etc., utilize burst clock techniques. A few illustrative examples which describe the use of a burst clock are provided in U.S. Pat. No. 4,561,442 to Vollmann et al., entitled "Implantable Cardiac Pacer With Discontinuous Microprocessor Programmable Anti Tachycardia Mechanisms and Patient Data Telemetry," issued Dec. 31, 1985; U.S. Pat. No. 5,022,395 to Russie, entitled "Implantable Cardiac Device With Dual Clock Control of Microprocessor," issued Jun. 11, 1991; U.S. Pat. No. 5,388, 578 to Yomtov et al., entitled "Improved Electrode System For Use With An Implantable Cardiac Patient Monitor," issued Feb. 14, 1995; and U.S. Pat. No. 5,154,170 to Bennett et al, entitled "Optimization for Rate Responsive Cardiac Pacemaker," issued Oct. 13, 1992.

FIG. 1 illustrates graphically energy/delay versus supply voltage for CMOS circuits such as CMOS inverter 10 shown in FIG. 2 for illustrative purposes. Inverter 10 is provided with a supply voltage, $V_{DD}$, which is connected to the source of a PMOS field effect transistor (FET) 12. PMOS FET 12 has its drain connected to the drain of an NMOS FET 14 whose source is connected to ground. In this configuration, an input $V_i$ applied to both the gates of FETs 12, 14 is inverted to provide output $V_o$. Simply stated, one clock cycle, or logic level change, is used to invert the input $V_i$ to $V_o$.

As shown in FIG. 1, the circuit logic delay increases drastically as the supply voltage is reduced to near one volt, as represented by delay line 16 and energy/delay line 18. As such, reducing of the supply voltage ($V_{DD}$) continuously to lower levels is impractical because of the need for higher supply voltages when higher frequency operation is required. For example, generally CMOS logic circuits must periodically provide functionality at a higher frequency, e.g., burst clock frequency. However, as the supply voltage ($V_{DD}$) is decreased, such energy consumption is reduced by the square of the supply voltage ($V_{DD}$) as is shown by energy consumption line 20. Therefore, speed requires a higher supply voltage ($V_{DD}$) which is in direct conflict with low power consumption.

Other problems are also evident when lower supply voltages ($V_{DD}$) are used for CMOS circuit designs. When a lower supply voltage is selected, static leakage current losses may arise, particularly at lower frequencies, due to increased static leakage current losses.

Various techniques for reducing power consumption in devices are known in the art, some examples of which may be found in the references listed in Table 1 below.

TABLE 1

| U.S. Pat. No. | Inventor | Issue Date |
| --- | --- | --- |
| 4,031,899 | Renirie | June 28, 1977 |
| 4,460,835 | Masuoka | July 17, 1984 |
| 4,561,442 | Vollmann et al. | December 31, 1985 |
| 4,791,318 | Lewis et al. | December 13, 1988 |
| 5,022,395 | Russie | June 11, 1991 |
| 5,154,170 | Bennett et al. | October 13, 1992 |
| 5,185,535 | Farb et al. | February 9, 1993 |
| 5,388,578 | Yomtov et al. | February 14, 1995 |
| 5,610,083 | Chan et al. | March 11, 1997 |

All references listed in Table 1 herein above are hereby incorporated by reference in their respective entireties. As those of ordinary skill in the art will appreciate readily upon reading the Summary of the Invention, Detailed Description of the Embodiments, and claims set forth below, at least some of the devices and methods disclosed in the present application, including those disclosed in the references listed in Table 1 hereinabove, may be modified advantageously in accordance with the teachings of the present invention.

SUMMARY OF THE INVENTION

The present invention has certain objects. That is, various embodiments of the present invention provide solutions to one or more problems existing in the prior art respecting circuitry design having lower Mower consumption, particularly with respect to implantable medical devices. Those problems include: CMOS, CML, SOS, SOI, BICMOS, PMOS and/or NMOS circuits having too large of a dynamic power consumption which reduces battery life; the inability to utilize low voltage supply levels effectively lack of ability to provide adequate processing capabilities such as high processing capabilities including telemetry uplink/downlink, morphology detection, initialization of devices, while still providing low processing capabilities such as sensing intrinsic beats, pacing. low speed telemetry, with the desired power consumption; and the inability to provide circuit designs that operate at lower frequencies and thus lower power consumption as opposed to the use of higher speed clocks such as burst clocks.

In comparison to known techniques for reducing power consumption in circuit designs, various embodiments of the present invention may provide one or more of the following advantages: reduced power consumption through the use of a lower voltage supply ($V_{DD}$); reduced power consumption by decreased clock frequency for circuit designs; increased longevity of circuits, particularly implantable device circuitry: provide a potential reduction in product size; minimize static leakage current losses, i.e., static power consumption: provide multi-processor designs, DSP designs, and high performance processing designs with additional features/function opportunities due to the ability to reduce power with respect to other "required" features and functions; and provide for substantial reduction in current drain.

Some embodiments of the invention include one or more of the following features: operation of circuits to complete a desired function (generally completed in a predetermined number of clock cycles) at a clock speed of a lower or intermediate level to adequately complete processing just-in-time prior to the next required functional process; using substantially an entire predetermined time period (e.g., one based on physiological events such as during a blanking interval, upper rate interval, escape interval, refractory interval, and pulse generator/programmer handshake, etc.) to perform a function at a clock speed such that the function is completed just prior to any next required functional process; providing one or more voltage sources or a voltage source operable to provide one or more supply voltages tailored for various circuit functions of a single integrated circuit; operatively connecting a clock source to two or more circuits such that different circuits are operated at different clock frequencies; adjusting supply voltage levels connected to one or more circuits based on the clock frequencies used for controlling operation of the circuits; adjusting back gate bias of a circuit based on the supply voltage level applied to the circuit; providing different supply voltage levels to processing circuitry depending upon the function being performed by the processing circuitry; operating processing circuitry at different clock frequencies depending upon the function being performed by the processing circuitry; changing the supply voltage level "on the fly" as required by specific circuit timing functions required for various circuit or processing circuitry functionality based an clock frequencies used to control operation of such circuitry; employing various ones or combinations of the foregoing features in CMOS, CML (Current Mode Logic), SOS (Silicon on Sapphire), SOI (Silicon on Insulator), BICMOS, PMOS and/or NMOS circuitry.

DETAILED DESCRIPTION OF THE PREFERRED EMBODIMENTS

The present invention is first generally described with reference to FIGS. 3 through 7. Thereafter, the present invention is described with reference to illustrative configurations of implantable medical devices shown in FIGS. 8 through 11.

Figure 1:
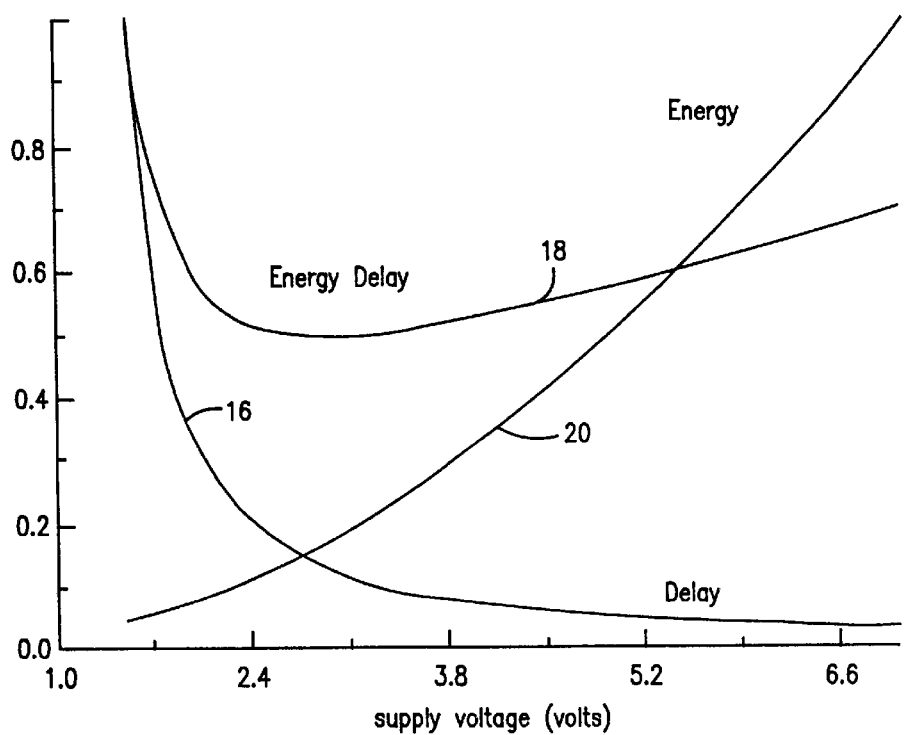
FIG. 1 is a graphical illustration showing energy/delay versus supply voltage for CMOS circuit operation.
Figure 2:
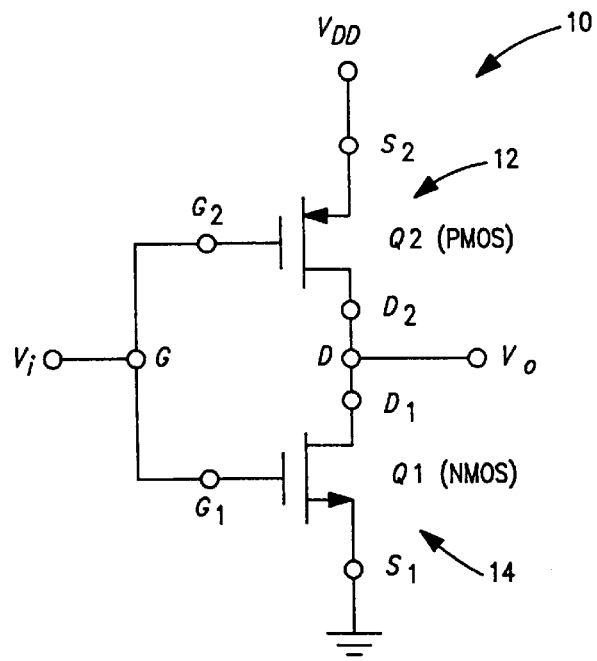
FIG. 2 shows a prior art CMOS inverter which is used as a building block in many CMOS circuit designs.
Figure 3:
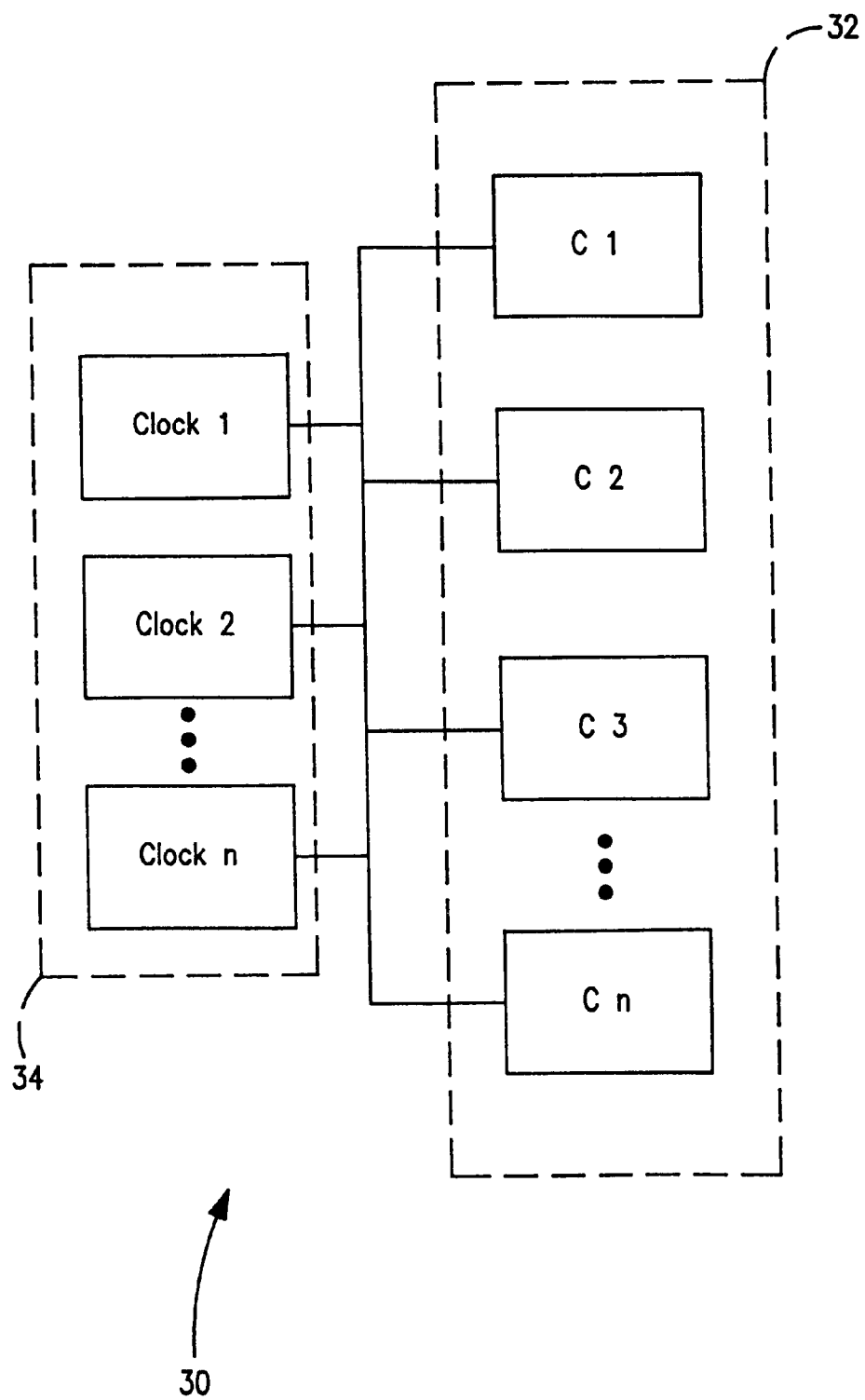
FIG. 3 is a block diagram of a just-in-time clocking system according to the present invention.

FIG. 3 shows a general block diagram of just-in-time clock system 30. Just-in-time clock system 30 includes integrated circuit 32 and clock source 34. Integrated circuit 32 includes a plurality of circuits C1–Cn. Each circuit when operable is capable of performing one or more circuit functions. A function is defined as any operation perform on one or more inputs in a plurality of cycles resulting in an output. Generally, the functions performed by the various circuits C1–Cn are performed in a predetermined number of clock cycles. Clock source 34 is operable for providing clock signals at a plurality of clock frequencies generally shown as clock1–clockn.

Circuits C1–Cn of integrated circuit 32 may include discrete function circuits (i.e., logic circuits for operating upon one or more inputs to implement a particular function to provide one or more outputs therefrom), such as circuits operating on one input from a sensor to provide a representative signal to further functional circuitry, transceiver circuitry, conversion circuitry, etc. Further, circuits C1–Cn may be data processing circuitry capable of performing multiple functions under program control or such circuits C1–Cn may implement firmware (software) functions/routines that must complete prior to some succeeding event or prior to the start of the next function. For example, as described further herein with respect to illustrative embodiments of implantable medical devices, such circuits may include digital signal processing circuits, circuitry used for telemetry uplink/downlink, morphology detection circuitry, arrhythmia detection circuitry, monitoring circuitry, pacing circuitry, microprocessors, etc.

The functions performed by each of the circuits C1–Cn are typically required to be completed in a particular time period prior to a next functional process being undertaken. For example, one logic circuit may perform a function in a predetermined time period to provide an output required by another circuit, or for example, a function may need to be performed by processing circuitry during a particular period of time due to the need for other processing to be performed by such processing circuitry. For example, in an implantable medical device, processing to complete a particular function may need to be performed in a portion of a particular time interval such as a blanking interval, an upper rate interval, an escape interval, or refractory interval of a cardiac cycle, or further, such as during a pulse generator/ programmer handshake.

Clock source 34 may be configured in any manner for providing clock signals at a plurality of frequencies. Such a clock source may include any number of clock circuits wherein each provides a single clock signal at a particular frequency, the clock source 34 may include one or more adjustable clock circuits for providing clock signals over a continuous range of clock frequencies, and/or the clock source 34 may include a clock circuit that is operable to provide clock signals at discrete clock frequencies as opposed to over a continuous range. For example, the clock source 34 may include oscillators, clock dividers, timers, clock control circuitry or any other circuit elements required for providing clock signaling according to the present invention. Preferably, clock source 34 is configured as a continuously oscillating low frequency clock and a controllable on/off higher frequency clock.

Figure 4A:
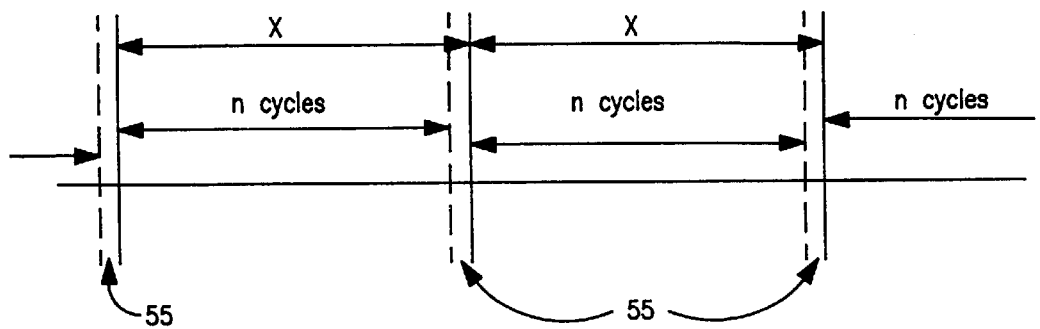
FIGS. 4A–4C show timing illustrations for use in describing the just-in-time clocking system of FIG. 3.
Figure 4B:
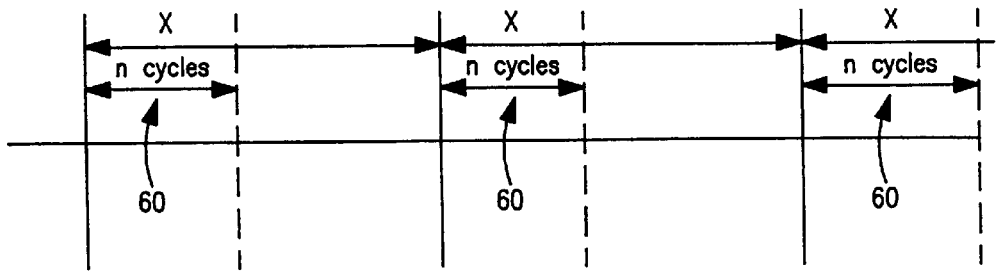

Just-in-time controllable clock operation of the just-in-time clocking system 30 of FIG. 3 shall be described with reference to FIGS. 4A–4C. As shown in FIG. 4A, time period (x) represents the time period in which a circuit, e.g., one of circuits C1–Cn, is required to complete one or more functions. The same time period (x) is shown in FIG. 4B. The time period x may be equated to any number of different time periods. For example, the time period may be the amount of time a processing circuit has to perform a particular detection function due to the need for a detection output by a certain point in time, may be a time period required to complete a particular function by a certain logic circuit so as to provide a timely output to a digital signal processing circuit, may be a time period to complete a firmware (software) routine, etc. Further, for example, the time period x may correspond to a cardiac cycle or a part thereof.

As shown in FIG. 4B, according to conventional processing, circuit functions were typically performed at a burst cycle frequency and, as such, the function performed required a time period 60. Therefore, only a small amount of time (i.e., time period 60) of the entire time period x was used to perform the one or more functions requiring n cycles of time to complete. In such a case, conventionally, such burst clocks were at a substantially high clock rate, e.g., 500–1000 KHz, for such short periods of time to gain the benefit of a "duty cycle" to reduce average current drain. However, such high clock rates may not be required for carrying out such functions, or all functions.

With just-in-time clocking according to the present invention, as shown in FIG. 4A, substantially the entire time period x is used to perform the one or more functions which are completed in n cycles. In other words, the clock frequency, e.g., one of clock1–clockn, for the circuit performing the one or more functions during the time period x is set such that the one or more functions are completed in the maximum time available for performing such functions, i.e., the clock frequency is at its lowest possible value. In other words, a lower frequency clock is used such that the one or more functions are performed just-in-time for other circuit or routine functionality to be performed. In such a just-in-time manner, the clock frequency used to control the performance of such functions by the particular CMOS, CML, SOS, SOI, BICMOS, PMOS and/or NMOS type of circuitry is lowered resulting in reduced power consumption by the circuitry. That is, according to the calculations of dynamic power, the lower frequency results in proportional power reduction. With the lowering of the clock frequency, the integrated circuit 32 including the various circuits C1–Cn can be designed to operate at a lower frequency, e.g., as opposed to burst frequency, and also at various other frequencies depending upon need.

Preferably, as used herein, use of the substantially entire predetermined period of time may result in a completion of the one or more functions being performed prior to the end of the time period x as is represented by remainder time periods 55 in FIG. 4A. This remainder time period 55, for example, is preferably near 0 seconds.

Figure 4C:
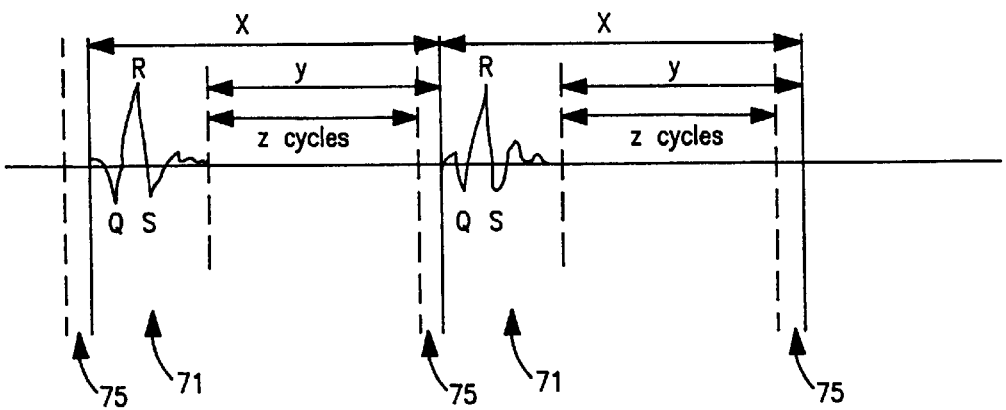

FIG. 4C shows an illustrative timing example for processing circuitry which performs multiple functions. For example, the cardiac cycle of a patient is represented in FIG. 4C as time period x. During time period 71, i.e., during a QRS complex of the cardiac cycle, high speed processing is performed at a high clock frequency relative to a lower clock frequency used to control operation of the processing circuitry during time period y. During the time period y, when the processing circuitry is operated at a lower clock frequency, such lower clock frequency may be set such that the functions performed during z cycles are performed in substantially the entire maximum time period available for such processing, i.e., time period y. Once again, a small remainder time period 75 of the cardiac cycle time period x may exist. Such time period may be, for example, in the range of about 1.0 millisecond to about 10.0 milliseconds when the cardiac cycle is in the range of about 400 milliseconds to about 1200 milliseconds.

Figure 5:
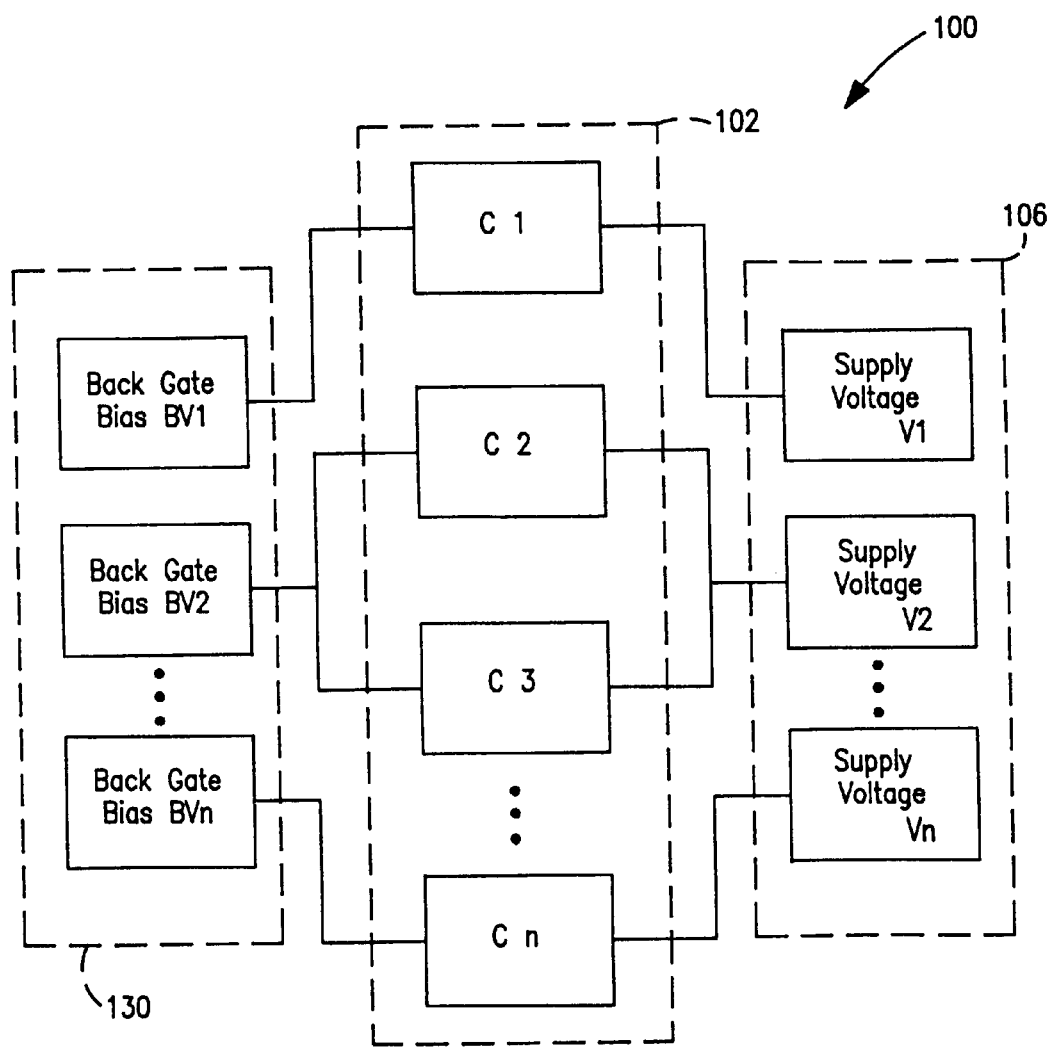
FIG. 5 is a block diagram illustration of a multiple supply voltage system according to the present invention.

FIG. 5 shows a general block diagram of a multiple supply voltage system 100 wherein one or more supply voltages are available and tailored for application to various circuits in an IC. The multiple supply voltage system 100 includes integrated circuit 102 and supply voltage source 106. Integrated circuit 102 includes circuits C1–Cn. Supply voltage source 106 is operable for providing a plurality of supply voltages V1–Vn. Each supply voltage from supply voltage source 106 is tailored to be applied to one or more circuits of circuits C1–Cn. As illustrated, supply voltage V1 is applied to circuit C1, supply voltage V2 is applied to circuit C2 and C3, and so forth.

The tailoring of the supply voltages V1–Vn to the particular circuits C1–Cn depends on the frequency at which the circuits C1–Cn are required to be operated. For example, and as previously described, the logic delay of such CMOS, CML, SOS, SOI, BICMOS, PMOS and/or NMOS circuits C1–Cn increases drastically as the supply voltage is reduced to near 1 volt. If such logic delay is tolerable, the supply voltage provided to a particular circuit will drastically reduce the power consumption for that particular circuit as the energy is reduced in proportion to the square of the supply voltage ($V_{DD}$). However, if such logic delay is not tolerable, for example, if the logic circuit performs a function that must be completed within a particular period of time, the reduction of the supply voltage ($V_{DD}$) applied to such a circuit will be limited depending upon the acceptable logic delay. However, the supply voltage $V_{DD}$ for any particular circuit can be reduced as low as possible yet meet adequate speed requirements.

Integrated circuit 102 may include various different circuits C1–Cn like those described with reference to FIG. 3. The supply voltage source 106 may be implemented using a variety of components and may include any number of voltage sources wherein each provides a single supply voltage level, may include one or more adjustable voltage sources for providing supply voltage levels over a continuous range of levels, and/or may include a voltage source that is operable to provide discrete supply voltage levels as opposed to levels over a continuous range. The supply voltage source may include a voltage divider, a voltage regulator, a charge pump, or any other elements for providing the supply voltages V1–Vn. Preferably, the supply voltage source 106 is configured as a charge pump.

Conventionally, supply voltage ($V_{DD}$) is generally in the range of about 3 volts to about 6 volts. Preferably, in accordance with the present invention, the supply voltages V1–Vn are in the range of about 1 volt to about 3 volts dependent upon the CMOS, CML, SOS, SOI, BICMOS, PMOS and/or NMOS type of technology used.

With reduction in supply voltage ($V_{DD}$), threshold voltage ($V_T$) for the circuits is also reduced. For example, with supply voltages in the range of about 3 to about 6 volts, the threshold voltage for CMOS, CML, SOS, SOI, BICMOS, PMOS and/or NMOS types of devices is generally in the range of about 0.8 volts to about 1.0 volt. Preferably, in implantable medical devices, lithium chemistries are utilized for implantable batteries. Such lithium chemistries are generally in the range of about 2.8 volts to about 3.3 volts and generally the CMOS, CML, SOS, SOI, BICMOS, PMOS and/or NMOS circuitry has an associated threshold voltage of about 0.75. By reducing the supply voltages below 2.8, the voltage thresholds for CMOS, CML, SOS, SOI, BICMOS, PMOS and/or NMOS devices may be decreased to as low as about 0.2 volts to about 0.3 volts.

Currently, there are various ultra low power logic designs operating at a supply voltage as low as about 1.1, e.g., such as logic designs for microprocessors for a laptop and other portable product designs. By utilizing the tailored supply voltages V1–Vn, low power or ultra low power logic designs may be used for at least some of the various circuits C1–Cn of integrated circuit 102. Other circuits may require supply voltages of a higher nature. With use of lower threshold levels due to lower supply voltages, static power consumption losses undesirably increase by several orders of magnitude.

Therefore, multiple supply voltage system 100 may further optionally include back gate bias source 130 for providing back gate bias voltages BV1–BVn to circuits C1–Cn of integrated circuit 102. Generally, the back gate bias voltages BV1–BVn are dependent upon the supply voltage V1–Vn applied to the circuits C1–Cn to adjust the threshold voltages for devices of circuits C1–Cn. For example, the threshold voltage ($V_T$) for the CMOS, CML, SOS, SOI, BICMOS. PMOS and/or NMOS devices of the circuit may be at a lower value by providing a back gate bias voltage to the particular circuits supplied with the lower supply voltage. Further, for example, if circuit C1 is supplied with a lower supply voltage V1, then a back gate bias voltage BV1 may optionally be applied to circuit C1 to adjust the threshold voltage ($V_T$) for the CMOS, CML, SOS, SOI, BICMOS, PMOS and/or NMOS devices to a higher threshold voltage ($V_T$) value. In this manner, static leakage current losses can be minimized because the equivalent higher threshold voltage has been restored. Further, a broader range of supply voltages is possible because the back gate adjustment allows a tailoring of the threshold allowing high/low speed operation and eliminating the static current drain leakage.

The back gate bias voltage may be provided by, for example, a fixed voltage source (i.e., a charge pump) connected to the back gate well via a contact. Alternatively, an active body bias scheme whereby the voltage source is selectable or adjustable over an appropriate range may be used.

Back gate voltages may be applied in any known manner. For example. the application of back gate bias voltages is described in various patent references including U.S. Pat. No. 4,791,318 to Lewis et al., U.S. Pat. No. 4,460,835 to Masuoka, U.S. Pat. No. 5,610,083 to Chan et al, and U.S. Pat. No. 5,185,535 to Farb et al., all incorporated by reference herein in their respective entireties.

Figure 6:
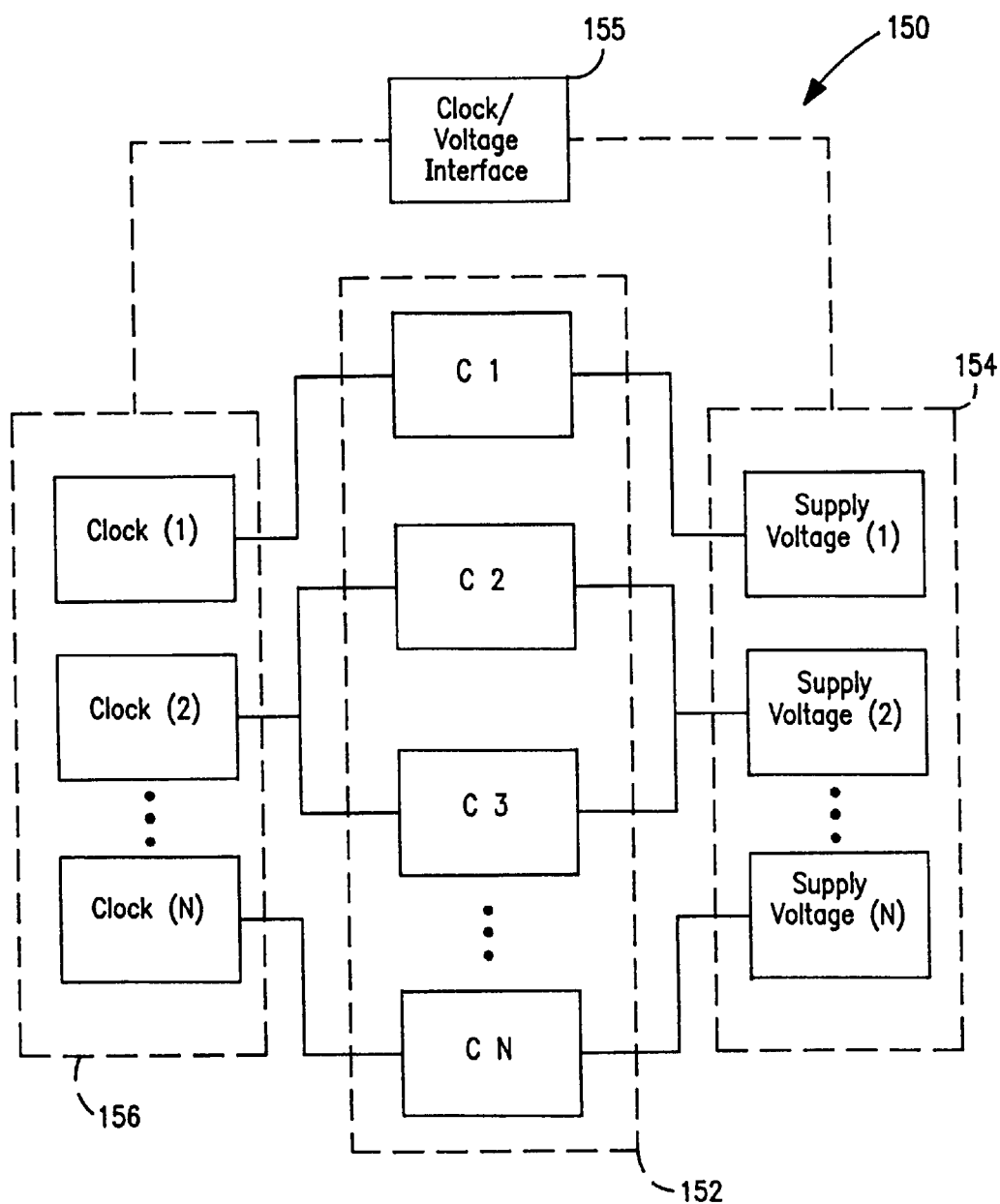
FIG. 6 is a block diagram illustrating a variable supply voltage system according to the present invention.

FIG. 6 shows a general block diagram of a variable supply voltage/variable clock system 150 according to the present invention. The system 150 includes integrated circuit 152, clock source 156, supply voltage source 154, and clock/supply voltage interface 155. Supply voltage source 154 is operable for providing a plurality of supply voltages V1–Vn to a plurality of circuits C1–Cn of integrated circuit 152. Further, the clock source 156 of system 150 is operable for providing clock signals at a plurality of frequencies, clock1–clockn. Circuits C1–Cn are of a similar nature to those described with reference to FIG. 3, the clock source 156 is similar to the clock source 34 as described with reference to FIG. 3, and the supply voltage source 154 is similar to the supply voltage source 106 as described with reference to FIG. 5. However, in the variable supply voltage/variable clock system 150, a clock/voltage interface 155 is used to adjust the supply voltages V1–Vn applied to the circuits C1–Cn "on the fly" as required by specific timing functions required by the circuits C1–Cn.

As an illustrative example, circuit C1 may be a particular logic circuit for performing one or more particular functions. However, such functions may be required to be performed in a first time period at a first clock frequency and during a different second time period at a second clock frequency to perform such function within the allowed time of the respective first and second time periods. In other words, one time period is shorter than the other and, as such, the functions which require performance over a certain number of cycles must be performed at a higher clock frequency if it is to be completed within a time period that is shorter than another time period. In such an example, according to the present invention, clock/voltage interface 155 detects the clock signal applied to circuit C1 during the first time period in which the higher frequency clock signal is used and accordingly provides supply voltage source 154 with a signal to select and apply a certain supply voltage corresponding to the higher clock frequency. Thereafter, when the lower clock frequency is applied to circuit C1 during the second time period, clock/voltage interface 155 senses the use of the lower clock frequency and applies a signal to voltage supply source 154 for application of a certain supply voltage corresponding to the lower clock frequency for application to circuit C1.

Figure 7:
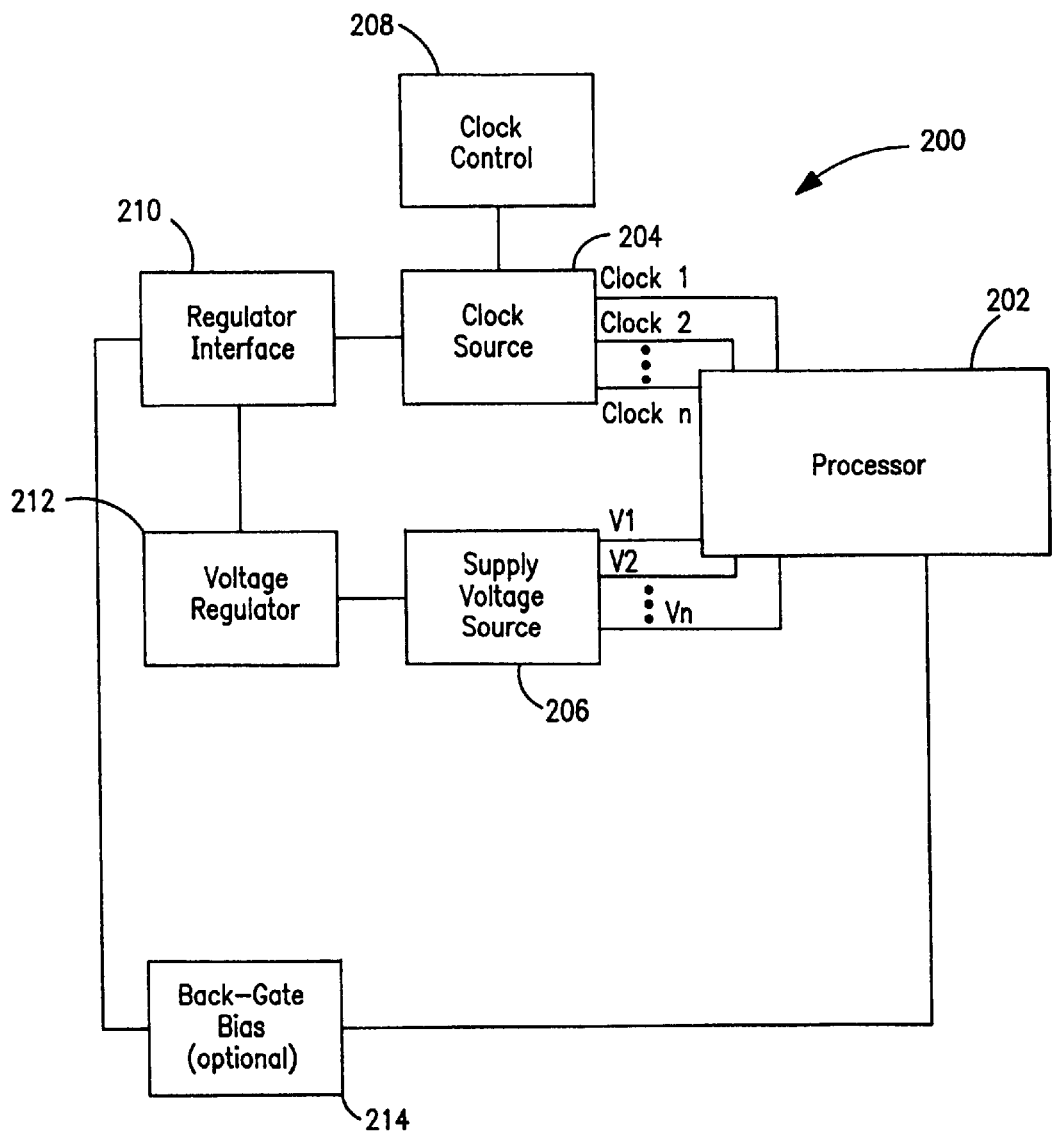
FIG. 7 is a block diagram of clock controlled processing circuitry according to the present invention.

Further, for example, circuit C2 may be a CMOS, CML, SOS, SOI, BICMOS, PMOS and/or NMOS type of processor which may also have clock frequency and corresponding supply voltage adjustments made "on the fly." Such a system will be readily apparent from the discussion to follow with reference to FIG. 7.

FIG. 7 shows a general block diagram of a clock controlled processing system 200 according to the present invention. The clock controlled processing system 200 includes processor 202 (e.g., a CMOS, CML, SOS, SOI, BICMOS, PMOS and/or NMOS type of microprocessor or CMOS, CML, SOS, SOI, BICMOS, PMOS and/or NMOS type of digital signal processor), clock source 204, supply voltage source 206, voltage regulator 212, regulator interface 210, clock control 208, and optional back gate bias source 214. In a manner similar to that described with reference to FIG. 6, the supply voltage 206 applied to processor 202 is changed "on the fly" as required by specific circuit timing requirements.

Generally, processor 202 is operated under control of clock source 204. Depending on the processing capability required, clock source 204 may operate processor 202 at any one of a plurality of clock frequencies. Such clock frequencies will be selected under the control of clock control 208. Clock control 208 may be part of any timing and control hardware and/or timing and control software used to control operation of processor 202 as part of a larger system. For example, such clock control may take the form of a digital controller/timer circuit for performing timing control of an implantable medical device.

Processor 202 may perform any number of functions as appropriate for the device in which it is used. High frequency processing capabilities (i.e., about 250 KHz to about 10 MHz), low frequency processing capabilities (i.e., about 1 Hz to about 32 KHz), and processing capabilities with regard to frequencies between such limits are contemplated according to the present to invention. For simplicity purposes, clock control processing system 200 operation is described with reference to processor 202 performing only two different functions, each during a predetermined respective period of time. For example, with respect to an implantable medical device such as a pacemaker, during the first period of time, a high processing function requiring a relatively high clock frequency may include a function such as telemetry uplink/downlink, morphology detection, initialization, arrhythmia detection, far-field R-wave detection, EMI detection, retrograde conduction, etc. On the other hand, low frequency processing functions may include a function such as sensing intrinsic beats, pacing, low speed telemetry, transtelephonic data transfer, remote monitoring, battery checks, etc.

When processor 202 during a predetermined time is to perform high frequency processing functions, a relatively high clock frequency, e.g. 250 KHz to 10 MHz, may be supplied by clock source 204 for operation of processor 202. Regulator interface 210 will detect the higher clock frequency applied to processor 202 for operation during the high processing function and apply a control signal to voltage regulator 212 for regulation of the supply voltage source 206. Supply voltage source 206 is operable under control of voyage regulator 212 to provide a supply voltage within a predetermined range, preferably between about 1.1 volts and about 3 volts. When a high clock frequency is used for operation of processor 202 for high frequency processing functions, supply voltage source 206 generally applies a supply voltage in the upper range of the preferred supply voltages to the CMOS, CML, SOS, SOI, BICMOS, PMOS and/or NMOS devices of processor 202.

On the other hand, when processor 202 is to execute low frequency processing functions during the predetermined periods of time, clock control 208 signals clock source 204 to apply a lower frequency for operation of processor 202. As such, regulator interface 210 detects the lower frequency being used to operate processor 202 and issues a control signal to voltage regulator 212 for regulation of supply voltage source 206 such that a lower supply voltage in the lower end of the preferred range of supply voltages is applied to the CMOS, CML, SOS, SOI, BICMOS, PMOS and/or NMOS devices of processor 202.

It will be recognized by those skilled in the art that any intermediate processing capability may be achieved between the higher frequency and the lower frequency capabilities described above and that the present invention is in no manner limited to processing at only two clock frequencies and at two corresponding supply voltages. Rather, multiple levels of processing capability can be achieved according to the present invention with associated clock frequencies and corresponding supply voltages being applied to processor 202.

FIG. 4C illustrates one embodiment of the clock control processing system 200. As shown therein, during the overall cardiac cycle of predetermined time period x, a high frequency is used for controlling operation of processor 202 during time period 71 of the cardiac cycle time period x, e.g., during processing of the QRS complex. Thereafter, a lower clock frequency is used during time period y for controlling operation of processor 202 to perform any of a number of other different functions, such as cardiac event/EMI differentiation functions. During operation of the processor 202 at the higher clock frequency during time period 71, a higher supply voltage from supply voltage source 206 is applied to the CMOS, CML, SOS, SOI, BICMOS, PMOS and/or NMOS devices of processor 202. Likewise, during operation of the processor 202 at the relatively lower clock frequency, a lower supply voltage from supply voltage source 206 is applied to the CMOS or other types of devices of processor 202 during time period y of the overall cardiac cycle time period x.

Further, as shown in FIG. 7, an optional back gate bias 214 may be used to dynamically adjust the threshold voltage ($V_T$) of CMOS, CML, SOS, to SOI, BICMOS, PMOS and/or NMOS devices of processor 202 as a function of the clock frequency applied to processor 202 by cock source 204. The regulator interface 210 detects the clock frequency used to control operation of processor 202 and controls the voltage level of back gate bias 214 to be applied to the CMOS, CML, SOS, SOI, BICMOS, PMOS and/or NMOS devices of processor 202. The dynamic adjustment of the threshold voltage may be implemented as an adjustable or selectable voltage source utilizing, for example, a charge pump and a regulator. The back gate voltage and the "normal" gate voltage provide a gate bias or voltage to the transistor. By adjusting the back gate voltage, the "apparent" voltage is increased with a resultant reduction in leakage current.

Figure 8:
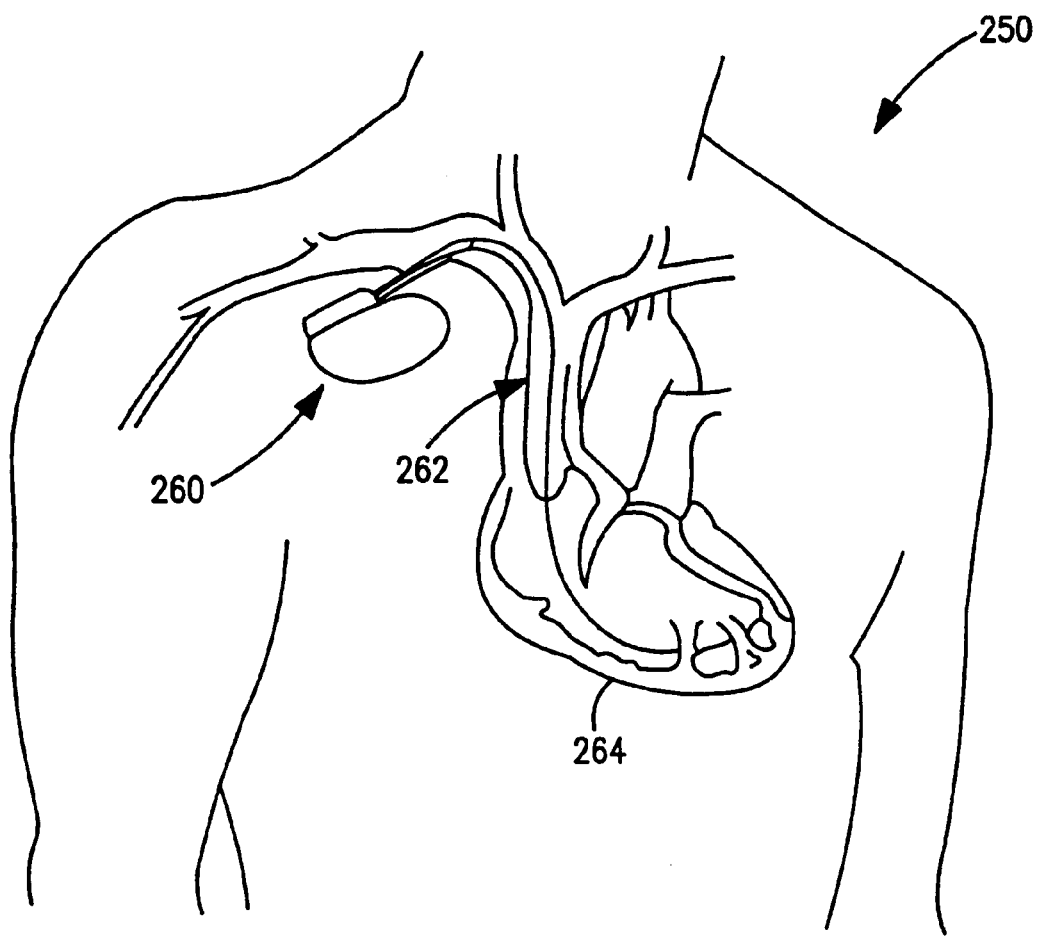
FIG. 8 is a diagram illustrating an implantable medical device in a body.

FIG. 8 is a simplified diagram of implantable medical device 260 for which the present invention is useful. Implantable device 260 is implanted in a body 250 near a human heart 264. Implantable medical device 260 is connected to heart 264 by leads 262. In the case where device 260 is a pacemaker, leads 262 are pacing and sensing leads to sense electrical signals attendant to the depolarization and repolarization of the heart 264 and provide pacing pulses in the vicinity of the distal ends thereof. Implantable medical device 260 may be any implantable cardiac pacemaker such as those disclosed in U.S. Pat. No. 5,158,078 to Bennett et al., U.S. Pat. No. 5,312,453 to Shelton et al., or U.S. Pat. No. 5,144,949 to Olson, all hereby incorporated herein by reference in their respective entireties and which can all be modified according to the present invention.

Figure 10:
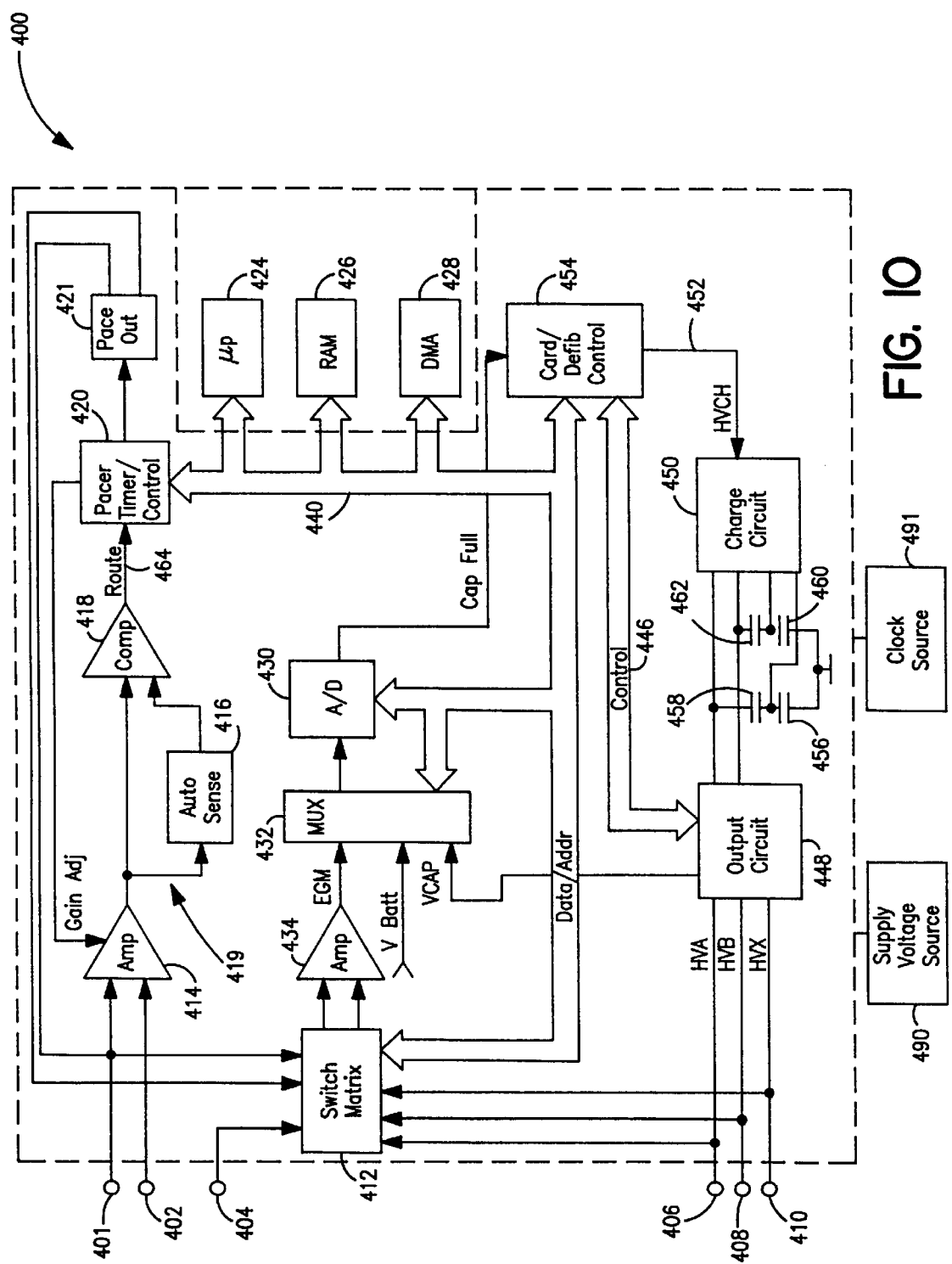
FIG. 10 is a schematic block diagram of an implantable pacemaker/cardioverter/defibrillator (PCD) for use in illustrating one or more embodiments of the present invention.

Implantable medical device 260 may also be a pacemaker/cardioverter/defibrillator (PCD) corresponding to any of the various commercially-available implantable PCDs, one of which is summarily described herein with reference to FIG. 10 and described in detail in U.S. Pat. No. 5,447,519. In addition to the PCD described in U.S. Pat. No. 5,447,519, the present invention may be practiced in conjunction with PCDs such as those disclosed in U.S. Pat. No. 5,545,186 to Olson et al., U.S. Pat. No. 5,354,316 to Keimel, U.S. Pat. No. 5,314,430 to Bardy, U.S. Pat. No. 5,131,388 to Pless, or U.S. Pat. No. 4,821,723 to Baker et al, all hereby incorporated herein by reference in their respective entireties. Those devices may be employed using the present invention in that such devices may employ or be modified with circuitry and/or systems according to the present invention.

Alternatively, implantable medical device 260 may be an implantable nerve stimulator or muscle stimulator such as those disclosed in U.S. Pat. No. 5,199,428 to Obel et al., U.S. Pat. No. 5,207,218 to Carpentier et al., or U.S. Pat. No. 5,330,507 to Schwartz, or an implantable monitoring device such as that disclosed in U.S. Pat. No. 5,331,966 issued to Bennet et al., all of which are hereby incorporated by reference herein in their respective entireties.

The present invention is believed to find wide application to any form of electrical device which uses CMOS, CML, SOS, SOI, BICMOS, PMOS, and/or NMOS devices, and is further believed to be particularly advantageous where low power consumption is desired, particularly in implantable medical devices.

At least some of the devices and methods disclosed in U.S. Pat. application Ser. No. 09/158,566 for "Cardiac Pacing System with Improved Physiological Event Classification based on DSP" to Wohigemuth filed Sep. 22, 1998 may also be advantageously modified in accordance with the teachings of the present invention. The foregoing '566 patent application is hereby incorporated by reference herein in its entirety.

In general, implantable medical device 260 includes a hermetically-sealed enclosure that includes an electrochemical cell such as a lithium battery, CMOS, CML, SOS, SOI, BICMOS, PMOS and/or NMOS circuitry that controls device operations, and a telemetry transceiver antenna and circuit that receives downlinked telemetry commands from and transmits stored data in a telemetry uplink to an external programmer. The circuitry may be implemented in discrete logic and/or may include a microcomputer-based system with AID conversion.

It is to be understood that the present invention is not limited in scope to particular electronic features and operations of particular implantable medical devices and that the present invention may be useful in conjunction with various implantable devices. Further, the present invention is not limited in scope to implantable medical devices including only a single processor but may be applicable to multiple-processor devices as well.

Figure 9:
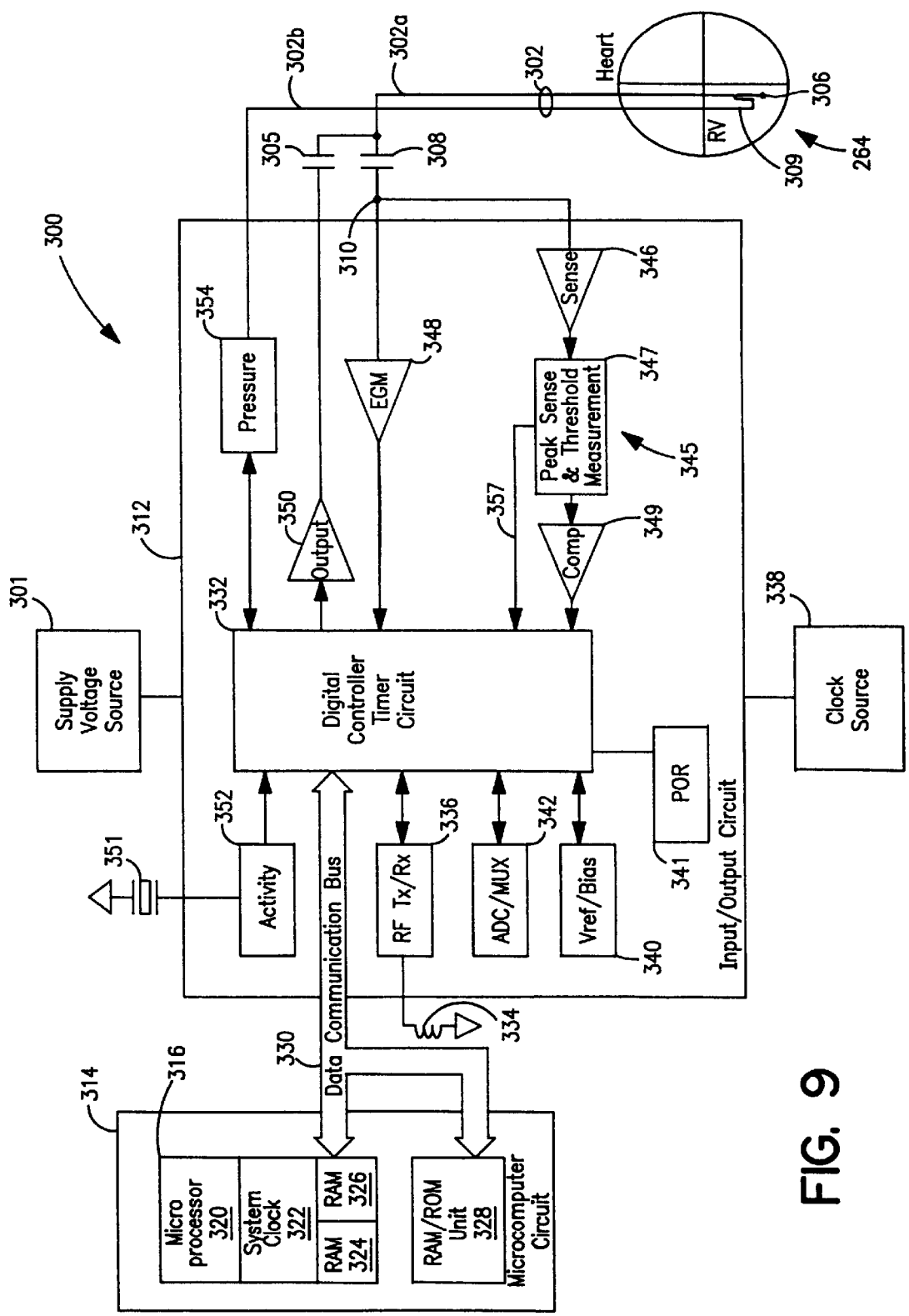
FIG. 9 is a block diagram of the circuitry of a pacemaker for use in illustrating one or more embodiments of the present invention.

FIG. 9 shows a block diagram illustrating the components of a pacemaker 300 in accordance with one embodiment of the present invention. Pacemaker 300 has a microprocessor-based architecture. However, the illustrative pacemaker 300 of FIG. 9 is only one exemplary embodiment of such devices and it will be understood that it could be implemented in any logic-based, custom integrated circuit architecture, if desired, as can any microprocessor-based system.

In the illustrative embodiment of FIG. 9, pacemaker 300 is most preferably programmable by means of an external programming unit (not shown in the figures). One such programmer suitable for the purposes of the present invention is the commercially available Medtronic Model 9790 programmer. The programmer is a microprocessor-based device which provides a series of encoded signals to pacemaker 300 by means of a programming head which transmits radio frequency (RF) encoded signals to antenna 334 of pacemaker 300 according to a telemetry system such as, for example, that described in U.S. Pat. No. 5,127,404 to Wyborny et al., the disclosure of which is hereby incorporated by reference herein in its entirety. It is to be understood, however, that any programming methodology may be employed so long as the desired information is transmitted to and from the pacemaker.

Pacemaker 300 illustratively shown in FIG. 9 is electrically coupled to heart 264 by leads 302. Lead 302a including electrode 306 is coupled to a node 310 in the circuitry of pacemaker 300 through input capacitor 308. Lead 302b is coupled to pressure circuitry 354 of input/output circuit 312 to provide a pressure signal from sensor 309 to the circuit 354. The pressure signal is used to ascertain metabolic requirements and/or cardiac output of a patient Further, activity sensor 351, such as a piezoceramic accelerometer, provides a sensor output to activity circuit 352 of input/output circuit 312. The sensor output varies as a function of a measured parameter that relates to metabolic requirements of a patient. Input/output circuit 312 contains circuits for interfacing to heart 264, to activity sensor 351, to antenna 334, to pressure sensor 309 and circuits for application of stimulating pulses to heart 264 to control its rate as a function thereof under control of software-implemented algorithms in microcomputer unit 314.

Microcomputer unit 314 preferably comprises on-board circuit 316 that includes microprocessor 320, system clock circuit 322, and on-board random access memory (RAM) 324 and read only memory (ROM) 326. In this illustrative embodiment, off-board circuit 328 comprises a RAM/ROM unit. On-board circuit 316 and off-board circuit 328 are each coupled by a communication bus 330 to digital controller/timer circuit 332.

According to the present invention, the circuits shown in FIG. 9 are powered by an appropriate implantable battery supply voltage source 301 (e.g., a voltage source generally shown in FIGS. 1–7). For the sake of clarity, the coupling of supply voltage source 301 to various circuits of pacemaker 300 is not shown in the figures. Further, the circuits operable under control of a clock signal shown in FIG. 9 are operated according to the present invention under clock source 338. For the sake of clarity, the coupling of such clock signals from the clock source 338 (e.g., a clock source generally shown in FIGS. 1–7) to such CMOS, CML, SOS, SOI, BICMOS, PMOS and/or NMOS circuits of pacemaker 300 is not shown in the Figures.

Antenna 334 is connected to input/output circuit 312 to permit uplink/downlink telemetry through RF transmitter ard receiver unit 336. Unit 336 may correspond to the telemetry and program logic disclosed in U.S. Pat. No. 4,556,063 issued to Thompson et al., hereby incorporated by reference herein in its entirety, or to that disclosed in the above-referenced Wybomy et al. patent.

$V_{REF}$ and bias circuit 340 generates a stable voltage reference and bias currents for circuits of input/output circuit 312. Analog-todigital converter (ADC) and multiplexer unit 342 digitize analog signals and voltages to provide "real-time" telemetry intracardiac signals and battery end-of-life (EOL) replacement function. A power on reset circuit 341 functions as a means to reset circuitry.

Operating commands for controlling the timing of pacemaker 300 are coupled by bus 330 to digital controller/timer circuit 332, where digital timers and counters establish the overall escape interval of pacemaker 300 as well as various refractory, blanking, and other timing windows for controlling the operation of the peripheral components disposed within input/output circuit 312.

Digital controller/timer circuit 332 is preferably coupled to sense circuitry 345 and to electrogram (EGM) amplifier 348 for receiving amplified and processed signals sensed by electrode 306 disposed on lead 302a. Such signals are representative of the electrical activity of the patient's heart 264. Sense amplifier 346 of circuitry 345 amplifies sensed electrocardiac signals and provides an amplified signal to peak sense and threshold measurement circuitry 347. Circuit 347 in turn provides an indication of peak sensed voltages and measured sense amplifier threshold voltages on path 357 to digital controller/timer circuit 332. An amplified sense amplifier signal is also provided to comparator/threshold detector 40. Sense amplifier 332 may correspond to that disclosed in U.S. Pat. No. 4,379,459 to Stein, which is hereby incorporated by reference herein in its entirety.

The electrogram signal provided by EGM amplifier 348 is employed when the implanted device 300 is being interrogated by an external programmer (not shown) to transmit by uplink telemetry a representation of an analog electrogram of the patient's electrical heart activity. Such functionality is, for example, shown in U.S. Pat. No. 4,556,063 to Thompson et al., previously incorporated by reference.

Output pulse generator and amplifier 350 provides pacing stimuli to heart 264 through coupling capacitor 305 and electrode 306 in response to a pacing trigger signal provided by digital controller/timer circuit 332. Output amplifier 350 may correspond generally to the output amplifier disclosed in U.S. Pat. No. 4,476,868 to Thompson, also incorporated by reference herein in its entirety. The circuits of FIG. 9 may be CMOS, CML, SOS, SOI, BICMOS, PMOS and/or NMOS circuitry capable of operating according to the present invention, and include processor 320, digital controller timer circuit 332, RAM 324, ROM 326, RAM/ROM unit 328 and ADC/Mux 342.

FIG. 10 is a functional schematic diagram from U.S. Pat. No. 5,447,519 to Peterson, which shows an implantable PCD 400 In which the present invention may usefully be practiced. This diagram is an illustration to be taken only as an exemplary type of device in which the invention may be embodied, and not as limiting to the scope of the present invention. Other implantable medical devices as previously described having functional organizations wherein the present invention may be useful may also be modified in accordance with the present invention. For example, the present invention is also believed to be useful in conjunction with implantable PCDs as disclosed in prior U.S. Pat. No. 4,548,209 to Wielders et al.; U.S. Pat. No. 4,693,253 to Adams et al.; U.S. Pat. No. 4,830,006 to Haluska et al.; and U.S. Pat. No. 4,949,730 to Pless et al.; all of which are incorporated herein by reference in their entireties.

Illustrative PCD 400 is provided with six electrodes 401, 402, 404, 406, 408, and 410. For example, electrodes 401 and 402 may be a lair of closely-spaced electrodes positioned in the ventricle of the heart 264. Electrode 404 may correspond to a remote, indifferent electrode located on the housing of the implantable PCD 400. Electrodes 446, 408, and 410 may correspond to large surface area defibrillation electrodes located on leads to the heart 264 or epicardial electrodes.

Electrodes 401 and 402 are shown as hard-wired to the near field (i.e. narrowly spaced electrodes) R-wave detector circuit 419 comprising band pass filtered amplifier 414, auto threshold circuit 416 (for providing an adjustable sensing threshold as a function of the measured R-wave amplitude), and comparator 418. Rout signal 464 is generated whenever the signal sensed between electrodes 401 and 402 exceeds a sensing threshold defined by auto threshold circuit 416. Further, the gain on amplifier 414 is adjusted by pacer timer and control circuitry 420. The sense signal, for example, is used to set the timing windows and to align successive waveshape data for morphology detection purposes. For example, the sense event signal 464 may be routed through the pacer/timer control circuit 420 on bus 440 to processor 424 and may act as an interrupt for the processor 424 such that a particular routine of operations, e.g., morphology detection, discrimination functions, is commenced by processor 424.

Switch matrix 412 is used to select available electrodes under control of processor 424 via data/address bus 440 such that the selection includes two electrodes employed as a far field electrode pair (i.e., widely spaced electrodes) in conjunction with a tachycardiaifibrillation discrimination function (e.g., a function to discriminate between tachycardia, i.e., an abnormally fast heart rate, and fibrillation, i.e., uncoordinated and irregular heartbeats, so as to apply an lo appropriate therapy). Far field EGM signals from the selected electrodes are passed through band pass amplifier 434 and into multiplexer 432, where they are converted to digital data signals by analog to digital converter (ADC) 430 for storage in random access memory 426 under control of direct memory access circuitry 428. For example, a series of EGM complexes for several seconds may be performed.

According to the present invention, the circuits shown in FIG. 10 are powered by appropriate implantable battery supply voltage source 490 (e.g., a voltage source generally shown in FIGS. 1–7). For the sake of clarity, the coupling of supply voltage source 490 to various circuits of PCD 400 is not shown in the figures. Further, the circuits operable under control of a clock signal shown in FIG. 10 are operated according to the present invention under clock source 491. For the sake of clarity, the coupling of such clock signals from the clock source 491 (e.g., a clock source generally shown in FIGS. 1–7) to such CMOS, CML, SOS, SOI, BICMOS, PMOS and/or NMOS circuits of PCD 400 is not shown in the Figures.

The occurrence of an R-wave sense event or detect signal Rout 464 is communicated to processor 424 to initiate morphology analysis on waveforms by processor 424 for use in selection of a therapy for heart 264. For example, the processor may calculate the cumulative beat-to-beat variability of heart 264, time intervals separating R-wave sense events, and various other functions as set out in numerous references including any of the references already listed herein and various other references with regard to implantable PCDs.

Other portions of PCD 400 of FIG. 10 are dedicated to the provision of cardiac pacing, cardioversion, and defibrillation therapies. With regard to cardiac pacing, the pacer timing/control circuit 420 includes programmable digital counters which control the basic timing intervals associated with cardiac pacing, including the pacing escape intervals, the refractory periods during which sensed R-waves are ineffective to restart timing of escape intervals, etc. The durations of such intervals are typically determined by processor 424 and communicated to pacer timer/control circuit 420 via address/data bus 440. Further, under control of processor 424, pacer timing/control circuit also determines the amplitude of such cardiac pacing pulses and pace out circuit 421 provides such pulses to the heart.

In the event that a tachyarrhythmia (i.e., tachycardia) is detected, and an anti-tachyarrhythmia pacing therapy is desired, appropriate timing intervals for controlling generation of anti-tachycardia pacing therapies are loaded from processor 424 into pacer timing and control circuitry 420. Similarly, in the event that generation of a cardioversion or defibrillation pulse is required, processor 424 employs the counters and timing and control circuitry 420 to control timing of such cardioversion and defibrillation pulses.

In response to detection of fibrillation or a tachycardia requiring a cardioversion pulse, processor 424 activates cardioversion/defibrillation control circuitry 454, which initiates charging of the high voltage capacitors 456, 458, 460 and 462 via charging circuit 450 under control of high voltage charging line 452. Thereafter, delivery of the timing of the defibrillation or cardioversion pulse is controlled by pacer timing/control circuitry 420. Various embodiments of an appropriate system for delivering and synchronization of cardioversion and defibrillation pulses, and controlling the timing functions related to them is disclosed in more detail in U.S. Pat. No. 5,188,105 to Keimel, which is incorporated herein by reference in its entirety. Other such circuitry for controlling the timing and generation of cardioversion and defibrillation pulses is disclosed in U.S. Pat. No. 4,384,585 to Zipes, U.S. Pat. No. 4,949,719 to Pless et al., and in U.S. Pat. No. 4,375,817 to Engle et al., all incorporated herein by reference in their entireties. Further, known circuitry for controlling the timing and generation of anti-tachycardia pacing pulses is described in U.S. Pat. No. 4,577,633 to Berkovits et al., U.S. Pat. No. 4,880,005 to Pless et al., U.S. Pat. No. 4,726,380 to Vollmann et al., and U.S. Pat. No. 4,587,970 to Holley et al., all of which are incorporated herein by reference in their entireties.

Selection of a particular electrode configuration for delivery of the cardioversion or defibrillation pulses is controlled via output circuit 448 under control of cardioversion/defibrillation control circuit 454 via control bus 446. Output circuit 448 determines which of the high voltage electrodes 406, 408 and 410 will be employed in delivering the defibrillation or cardioversion pulse regimen.

The components of PCD 400 of FIG. 10 may be CMOS, CML, SOS, SOI, BICMOS, PMOS and/or NMOS circuitry capable of operation according to the present invention include processor 424, control circuits 420 and 454, RAM 426, DMA 428, ADC 430, and multiplexer 432.

According to the present invention, pacemaker 300 illustrated in FIG. 9 and PCD 400 illustrated in FIG. 10 may both be implemented in accordance with the generalized embodiments previously described herein with reference to FIGS. 1–7. First, for example, with respect to pacemaker 300 of FIG. 9, the voltage supply source 301 of pacemaker 300 may be implemented in a manner previously described with reference to FIGS. 1–7 and, likewise, clock source 338 of pacemaker 300 may be implemented in such a manner as described with reference to FIGS. 1–7. Likewise, clock source 491 of PCD 400 of FIG. 10 and the voltage supply source 490 of PCD 400 of FIG. 10 may be implemented in accordance with the generalized embodiments previously described herein with reference to FIGS. 1–7.

As one illustrative example, ADC/mux 342, the RF transmitter/receiver 336, digital controller timer circuit 332, and various other CMOS circuits may be individually operated at different clock frequencies available from clock source 338. Likewise, such circuits may be operated at corresponding supply voltages which may be different for each of the circuits. Further, for example, RF transmitter/receiver 336 may be operated during a particular time period (e.g., when uplinking) at a particular clock frequency available from clock source 338 and at a particular supply voltage available from voltage supply source 301 corresponding to the particular clock frequency. On the other hand, during a different time period (e.g., during downlink), the circuit 336 may be operated at a completely different clock frequency and supply voltage. Automatic adjustment of telemetry parameters under certain circumstances is described in U.S. Pat. No. 5,683,432 to Goedeke et al.

Additionally, and in respect of FIG. 10, A/D converter circuit 430, cardioverter/defibrillator control circuit 454, and various other circuits such as RAM 426, DMA 428, and multiplexer 432 may also be operated at different clock frequencies available from clock source 491 and at different corresponding supply voltages available from supply voltage source 490. Further, a telemetry circuit (not shown) may be used with PCD 400 of FIG. 10 and may also be operated at different clock frequencies available from clock source 491 and at different corresponding supply voltages available from supply voltage source 490. In addition, processor 424 may be operated at different clock speeds depending upon the function being performed by the processor 424, such as described with reference to FIG. 7 herein. For example, morphology detection sensing at typical physiologic rates (i.e., 50 to 150 BPM) may be performed at a first clock frequency and corresponding supply voltage while arrhythmia detection may be performed at a different clock frequency and corresponding supply voltage.

Figure 11:
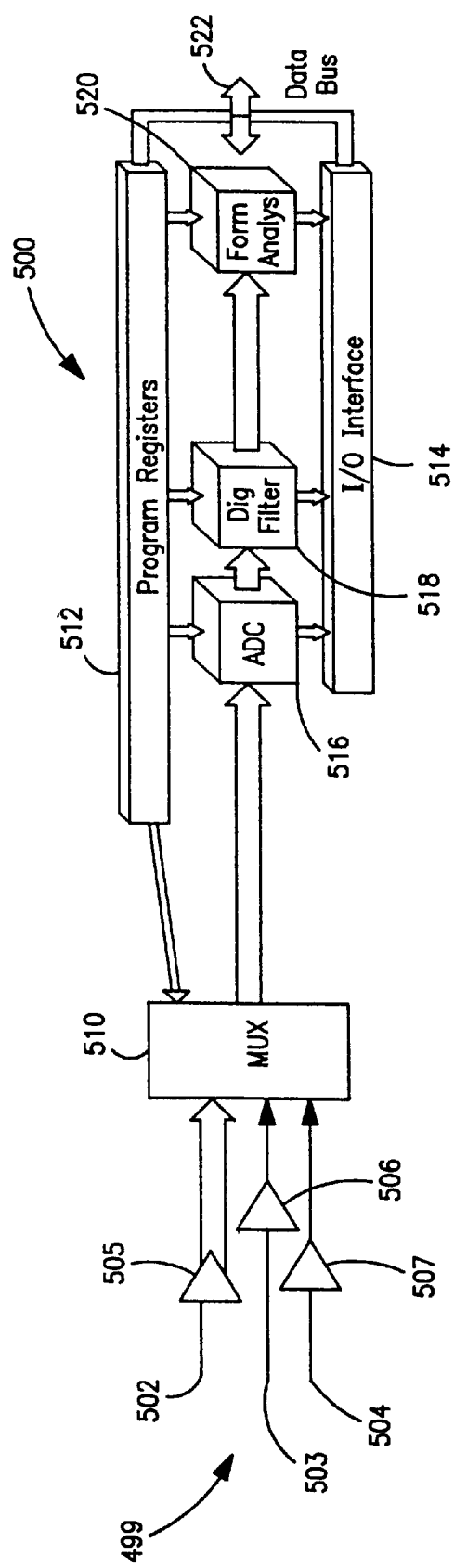
FIG. 11 is a schematic block diagram illustrating a variable clock/variable supply voltage digital signal processing system according to the present invention.

FIG. 11 shows a variable clock/variable supply voltage digital signal processing system 500 which may be used in conjunction with and/or in the alternative to certain circuits shown in FIGS. 9 and 10. For example, the digital signal processing system 500 according to FIG. 11 may be used in place of activity circuit 352, pressure circuit 354, sense amplifier circuit 346 (for P-wave, R-wave- and/or T-wave sense amplifiers), and further may be provided with additional functionality with use of a pseudo EKG signal 502. Generally, any number of analog signals 499, for example, such as pseudo EKG signals 502, activity sensor signal 503 and pressure and onset sensor signal 504, are provided through respective amplifiers 505–507. The amplified signals are presented to multiplexer 510 which provides them to analog to digital converter (ADC) 516 in a cycled fashion. The signals 502–504 can be cycled at different rates by cycling through the outputs of the several amplifiers/preamplifiers 505–507 such as described in pending U.S. Pat. application Ser. No. 08/801,335, entitled "Method for Compressing Digitized Cardiac Signals Combining Lossless Compression and Non-linear Sampling," which describes variable compression via ADC sampling and which is incorporated herein by reference in its entirety. The ADC may also have variable conversion rates as described in U.S. Pat. No. 5,263,486 and U.S. Pat. No. 5,312,446 which are also incorporated herein by reference in their entireties.

Input/output interface 514 and program registers 512 are utilized under control of a timing circuit (not shown) to control application of the analog signals from multiplexer 510 to ADC 516 which provides such converted digital signals to digital filter 518 to provide a waveform for analysis to waveform analysis processor 520 (i.e., a digital signal processor (DSP)). To reduce power, the waveform analysis processor 520 is clocked at different speeds, i.e., controlled "on the fly," according to the present invention, depending upon the processing needs.

For example, only during a QRS complex will the waveform analysis processor 520 be in a high speed processing mode at a relatively high frequency, while during the remainder of the cardiac cycle the processor 520 may be "idling along" at a much lower clock frequency. Such a processing cycle has been previously described with reference to FIG. 4C. In addition to the lower clock speed utilized for different portions of the cardiac cycle, one skilled in the art will recognize that in accordance with the other aspects of the present invention, as the speed is reduced, the supply voltage level ($V_{DD}$) may also be reduced accordingly. Thus, reduced power consumption is attained as previously described.

The present invention is compatible with various fabrication technologies, including but not limited to, silicon on insulator (SOI), silicon on sapphire (SOS), current mode logic (CML), BICMOS, PMOS and NMOS technologies, as well as conventional silicon CMOS technologies. U.S. Pat. Nos. 4,359,653 to Takamasa; 5,416,043 to Burgener et al.: 5,538,908 to Kim; 5,705,421 to Matsushita et al., all hereby incorporated herein by reference, each in its respective entirety, describe integrated circuit fabrication processes and methods of use for at least some of the foregoing integrated circuit types.

The present invention permits the use of DSPs to perform more functions than might otherwise be possible owing to the manner in which power consumption may be reduced in such DSPs. Furthermore, multiple processor based designs may also be implemented due to reduced power consumption as supply voltages and clocking frequencies are reduced for various functions performed by the processors.

Additionally, as power consumption is reduced, further functionality may be added to devices to provide a device with added functionality relative to previously higher consuming devices. A processor may, for example, perform various morphology detection functions such as differentiation of retrograde P-waves and antegrade P-waves of EGM waveform; differentiation of P-waves from far field R-waves; differentiation of AF-A flutter-AT from sinus tachycardia; differentiation of VT-VF-V flutter from SVT; differentiation of cardiac signals from electromagnetic interference; etc. For example, electromagnetic interference (EMI) may be apparent from theft detectors, conductive signals. RF noise, myopotentials, etc.

The preceding specific embodiments are illustrative of the practice of the invention. It is to be understood, therefore, that other expedients known to those skilled in the art or disclosed herein may be employed without departing from the invention or the scope of the appended claims. The present invention is not limited, for example, to the use of a clock source for providing discrete clock frequencies. Instead, such clock frequencies may be varied in a continuous manner. Moreover, the supply voltage source may include not only discrete supply voltages, but may include a source that is varied continuously over a particular range, such as, for example, by a voltage regulator. The present invention is also not limited to use in conjunction with pacemakers or PCDs, but may find further application in other relevant areas such as telecommunications or portable computers where low power consumption is desired. The present invention further includes within its scope methods of making and using the just-in-time clocking and/or multiple supply voltage concepts described herein above.

In the claims, mean plus function clauses are intended to cover the structures described herein as performing the recited function and their equivalents. Means plus function clauses in the claims are not intended to be limited to structural equivalents only, but are also intended to include structures which function equivalently in the environment of the claimed combination.

I claim:

1. A method of conserving power in a medical device, the method comprising:

providing processing circuitry operable for performing at least a first and second function;

operating the processing circuitry at a first supply voltage level to perform the first function;

operating the processing circuitry at a second supply voltage level to perform the second function, wherein the first supply voltage level is different from the second supply voltage level; and completing the first function just prior to the start of the second function.

2. The method of claim 1, wherein the first operating step includes operating the processing circuitry at a first clock frequency to perform the first function, and the second operating step includes operating the processing circuitry at a second clock frequency to perform the second function, and wherein the first clock frequency is different that the second clock frequency.

3. The method of claim 2, and further including:

determining the first supply voltage level based on the first clock frequency; and determining the second supply voltage level based on the second clock frequency.

4. The method of claim 2, wherein the first clock frequency is higher than the second clock frequency.

5. The method of claim 2, wherein the first clock frequency is higher than the second clock frequency.

6. The method of claim 5, wherein the first function is a function selected from the group of high speed telemetry uplink/downlink, morphology detection, device initialization, arrhythmia detection, far-field R-wave detection, EMI detection, and retrograde conduction.

7. The method of claim 5, wherein the second function is selected from the group of intrinsic heartbeat sensing, pacing, low speed telemetry, transtelephonic data, and batter check.

8. The method of claim 1, wherein the step of providing the processing circuitry further comprises the method of providing circuitry of at least one type selected from the group consisting of CMOS circuitry, CML circuitry, SOS circuitry, SOI circuitry, BICMOS circuitry, PMOS circuitry and NMOS circuitry.

9. The method of claim 1, further comprising the step of providing an hermetically sealed implantable medical device as said medical device.

10. The method of claim 9, wherein provision of the implantable medical device further comprises the step of providing an implantable medical device selected from the group consisting of an implantable stimulator, an implantable nerve stimulator, an implantable pacemaker, an IPG, an implantable cardioverter, an implantable PCD, an implantable defibrillator, an implantable ICD and an implantable drug pump.

* * * * *

UNITED STATES PATENT AND TRADEMARK OFFICE
CERTIFICATE OF CORRECTION

PATENT NO. : 6,324,426 B1 Page 1 of 1
DATED : November 27, 2001
INVENTOR(S) : David L. Thompson It is certified that error appears in the above-identified patent and that said Letters Patent is hereby corrected as shown below:

Column 19,
Line 8, delete "batter" and insert -- battery --.

Signed and Sealed this

Twenty-eighth Day of January, 2003

JAMES E. ROGAN
*Director of the United States Patent and Trademark Office*